United States Patent
Baaijens et al.

(10) Patent No.: US 9,491,833 B2
(45) Date of Patent: Nov. 8, 2016

(54) LIGHTING METHODS FOR PROVIDING PERSONALIZED LIGHTING TO USERS POSITIONED PROXIMAL TO ONE ANOTHER

(71) Applicant: KONINKLIJKE PHILIPS N.V., Eindhoven (NL)

(72) Inventors: Johannes Petrus Wilhelmus Baaijens, Eindhoven (NL); Lucas Josef Maria Schlangen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/438,460

(22) PCT Filed: Oct. 17, 2013

(86) PCT No.: PCT/IB2013/059426
§ 371 (c)(1),
(2) Date: Apr. 24, 2015

(87) PCT Pub. No.: WO2014/064587
PCT Pub. Date: May 1, 2014

(65) Prior Publication Data
US 2015/0289347 A1    Oct. 8, 2015

Related U.S. Application Data

(60) Provisional application No. 61/718,934, filed on Oct. 26, 2012.

(51) Int. Cl.
*H05B 37/02* (2006.01)
*H05B 39/04* (2006.01)
(Continued)

(52) U.S. Cl.
CPC ........ *H05B 37/0227* (2013.01); *H05B 39/044* (2013.01); *A61M 2021/0044* (2013.01); *A61N 5/06* (2013.01); *A61N 2005/0626* (2013.01)

(58) Field of Classification Search
CPC .......... F21Y 2101/02; F21Y 2105/00; F21Y 2103/003; F21K 9/13; F21K 9/56; F21K 9/50; F21K 9/52; H05B 37/0272; H05B 37/0227; H05B 33/0803; H05B 33/0815; H05B 33/0845; H05B 37/0281; H05B 33/0857
See application file for complete search history.

(56) References Cited

U.S. PATENT DOCUMENTS 7,564,368 B2    7/2009    Segall
7,843,353 B2    11/2010    Pan et al.
(Continued)

FOREIGN PATENT DOCUMENTS

DE    102010030501 A1    12/2010
EP    0677697 A    10/1995
(Continued)

*Primary Examiner* — Jany Richardson
(74) *Attorney, Agent, or Firm* — Meenakshy Chakravorty

(57) ABSTRACT

Methods for providing personalized lighting to users (102A, 102H) positioned proximal to one another. First lighting (103A, 106A) may be provided to a first user (102A) when the first user is not proximal any conflicting lighting users (102H). Second lighting (103A, 106A) may be provided to the first user (102A) when a first user lighting need is in conflict with a conflicting user (103H, 106H) lighting need of a conflicting user (102H) that is proximal the first user (102A). The second lighting (103A, 106A) may be set to minimize contrast with lighting supplied to the conflicting user.

19 Claims, 5 Drawing Sheets

(51) Int. Cl.
*A61N 5/06* (2006.01)
*A61M 21/00* (2006.01)

(56) References Cited

U.S. PATENT DOCUMENTS

| | | | |
|---|---|---|---|
| 7,845,823 B2 | 12/2010 | Mueller et al. | |
| 7,866,848 B2 | 1/2011 | Chen | |
| 8,035,320 B2 | 10/2011 | Sibert | |
| 2011/0282468 A1 | 11/2011 | Ashdown | |
| 2011/0307112 A1 | 12/2011 | Barrilleaux | |
| 2012/0184299 A1* | 7/2012 | Loveland | G05B 15/02 455/456.3 |
| 2015/0061506 A1* | 3/2015 | Baaijens | G02F 1/29 315/152 |
| 2015/0174361 A1* | 6/2015 | Baaijens | A61N 5/0618 315/131 |
| 2015/0296594 A1* | 10/2015 | Blum | H05B 37/0227 315/158 |

FOREIGN PATENT DOCUMENTS

| | | | |
|---|---|---|---|
| NL | WO 2010079388 A1 * | 7/2010 | H05B 37/0245 |
| WO | 2010079388 A1 | 7/2010 | |
| WO | 2011039688 A1 | 4/2011 | |

* cited by examiner

LIGHTING METHODS FOR PROVIDING PERSONALIZED LIGHTING TO USERS POSITIONED PROXIMAL TO ONE ANOTHER

CROSS-REFERENCE TO PRIOR APPLICATIONS

This application is the U.S. National Phase application under 35 U.S.C. §371 of International Application No. PCT/IB2013/059426, filed on Oct. 17, 2013, which claims the benefit of U.S. Provisional Patent Application No. 61/718,934, filed on Oct. 26, 2012. These applications are hereby incorporated by reference herein.

TECHNICAL FIELD

The present invention is directed generally to lighting control and lighting apparatus. More particularly, various inventive methods and apparatus disclosed herein relate to methods and apparatus for providing personalized lighting to users positioned proximal to one another.

BACKGROUND

Digital lighting technologies, i.e. illumination based on semiconductor light sources, such as light-emitting diodes (LEDs), offer a viable alternative to traditional fluorescent, HID, and incandescent lamps. Functional advantages and benefits of LEDs include high energy conversion and optical efficiency, durability, lower operating costs, and many others. Recent advances in LED technology have provided efficient and robust full-spectrum lighting sources that enable a variety of lighting effects in many applications. Some of the fixtures embodying these sources feature a lighting module, including one or more LEDs capable of producing different colors, e.g. red, green, and blue, as well as a processor for independently controlling the output of the LEDs in order to generate a variety of colors and color-changing lighting effects.

User-responsive lighting systems have been implemented where users carry a personal device that communicates their lighting needs to the lighting system. The light output of one or more lighting fixtures in the lighting environment may be adjusted in response to a users' lighting preferences based on their lighting needs. Although such systems enable adjustment of a lighting fixture based on the individual settings of a user, they have a number of drawbacks. For example, in some environments (e.g., social settings, discussion groups, and/or meeting rooms), a user may want to move as desired throughout the environment while still maintaining his or her lighting preferences. Some user-responsive lighting systems may not enable such freedom of movement while maintaining lighting preferences. Also, for example, in some environments where multiple users interact, users with differing lighting needs may not be supplied with individualized lighting zones that lessen contrast between the individualized lighting zones.

Various therapeutic lighting systems have also been implemented. Such therapeutic lighting systems often include a lighting fixture that a user must sit or stand in front of for a period of time for therapy purposes. Such therapeutic lighting systems may have one or more drawbacks such as, for example, the requirement of dedicated spaces or locations for use and/or the bright therapeutic light being bothersome to other individuals present nearby that have other lighting needs.

Thus, there is a need in the art to provide lighting methods and apparatus for providing personalized lighting to users positioned proximal to one another that optionally overcomes one or more drawbacks of other lighting applications and/or methods.

SUMMARY

The present disclosure is directed to inventive methods and apparatus for providing personalized lighting to users positioned proximal to one another. For example, first lighting may be provided to a first user when the first user is not proximal any conflicting lighting users. Second lighting may be provided to the first user when a first user lighting need is in conflict with a conflicting user lighting need of a conflicting user that is proximal the first user. The second lighting may be set to minimize contrast with lighting supplied to the conflicting user. For example, the second lighting may be more conforming to the conflicting user lighting need in light output intensity than the first lighting is to the conflicting user lighting. Also, for example, the second lighting may be more conforming to the conflicting user lighting need in color temperature than the first lighting is to the conflicting user lighting.

Generally, in one aspect, a method of providing individualized lighting settings in a lighting system is provided and includes the steps of: identifying first user lighting information indicative of first user lighting needs of a first user, the first user lighting needs indicative of a first light intensity at a reference color temperature and a first color temperature at a reference light intensity; identifying second user lighting information indicative of second user lighting needs of a second user, the second user lighting needs indicative of a second light intensity at the reference color temperature and a second color temperature at the reference light intensity; and providing a first lighting having a modified first light characteristic to the first user and simultaneously providing a second lighting having a second light characteristic to the second user when the first user and the second user are within a predefined distance and when variation between the first user lighting needs and the second user lighting needs is outside of a predefined variation. The modified first light characteristic includes at least one of a modified first light intensity and a modified first color temperature. The second light characteristic includes an actual second light intensity and an actual second color temperature. The first lighting and the second lighting satisfy either a first condition or a second condition, wherein in the first condition a modified light intensity absolute difference between the modified first light intensity and the actual second light intensity is less than an original light intensity absolute difference between the first light intensity and the second light intensity; and where in the second condition a modified color temperature absolute difference between the modified first color temperature and the actual second color temperature is less than an original color temperature absolute difference between the first color temperature and the second color temperature.

In some embodiments, the modified first light characteristic includes both the modified first light intensity and the modified first color temperature. In some versions of those embodiments the modified first color temperature is adjusted to maintain the first user lighting needs at the modified first light intensity.

In some embodiments, the first lighting includes a face first lighting component having a face first light intensity and a task first lighting component having a task first light intensity. In some versions of those embodiments the face first light intensity is closer to the first user lighting needs than the task first light intensity is to the first user lighting needs. In some versions of those embodiments the second lighting includes a face second lighting component having a face second light intensity and a task second lighting component having a task second light intensity. In some versions of those embodiments the face second light intensity is closer to the second user lighting needs than the task second light intensity is to the second user lighting needs. In some versions of those embodiments a face absolute difference between the face first light intensity and the face second light intensity is greater than a task absolute difference between the task first light intensity and the task second light intensity.

In some embodiments, the first lighting includes a face first lighting component having a face first color temperature and a task first lighting component having a task first color temperature, wherein the second lighting includes a face second lighting component having a face second color temperature and a task second lighting component having a task second color temperature, and wherein the face first color temperature is more conforming to the face second color temperature than the task first color temperature is to the task second color temperature.

In some embodiments, the first lighting is provided on an intermittent basis.

In some embodiments, the method further includes identifying a first user position, identifying a second user position, and comparing the first user position to the second user position to determine the predefined distance.

In some embodiments, in the first condition the modified color temperature absolute difference between the modified first color temperature and the modified second color temperature is greater than the original color temperature absolute difference between the first color temperature and the second color temperature. In some versions of those embodiments, in the second condition the modified light intensity absolute difference between the modified first light intensity and the actual second light intensity is greater than the original light intensity absolute difference between the first light intensity and the second light intensity.

In some embodiments, in the second condition the modified light intensity absolute difference between the modified first light intensity and the actual second light intensity is greater than the original light intensity absolute difference between the first light intensity and the second light intensity.

Generally, in another aspect, a method of providing individualized lighting settings in a lighting system is provided and includes the steps of: identifying a first lighting to provide to a first user when the first user is not proximal any conflicting lighting users, the first lighting conforming to a first user lighting need of the first user and having a first lighting light output intensity and a first lighting color temperature; and providing second lighting to the first user when the first user lighting need is in conflict with a conflicting user lighting need of a conflicting user that is proximal the first user, the second lighting having a second lighting light output intensity that is more conforming to light output intensity of the conflicting user lighting need than the first lighting light output intensity is to the light output intensity of the conflicting user lighting need.

In some embodiments, the second lighting has a second lighting color temperature that is less conforming to the color temperature of the conflicting user lighting need than the first color temperature is to the color temperature of the conflicting user lighting need.

In some embodiments, the second lighting includes a face first lighting component having a face first light intensity and a face first color temperature and a task first lighting component having a task first light intensity and a task first color temperature. In some versions of those embodiments the task first light intensity is more conforming to the light output intensity of the conflicting user lighting need than the face first light intensity is to the light output intensity of the conflicting user lighting need. In some versions of those embodiments the task first color temperature is more conforming to the color temperature of the conflicting user lighting need than the face first color temperature is to the light output intensity of the conflicting user lighting need.

In some embodiments, the second lighting is provided after the first user and the conflicting user are within a predefined distance of one another for a predefined amount of time.

In some embodiments, the second lighting is provided on an intermittent basis. Also, the second lighting may have a spectral power distribution that is increased in at least one of the blue-green region and the yellow-red region relative to the first lighting.

In some embodiments, the method further includes the step of setting the second lighting color temperature of the second lighting to achieve the first user lighting need at the second lighting light output intensity.

Generally, in another aspect, a method of providing individualized lighting settings in a lighting system is provided and includes the steps of: identifying first lighting to provide to a first user when the first user is not proximal any conflicting lighting users, the first lighting conforming to a first user lighting need of the first user and having a first lighting light output intensity and a first lighting color temperature; and providing second lighting to the first user when the first user lighting need is in conflict with a conflicting user lighting need of a conflicting user that is proximal to the first user, the second lighting having a second lighting color temperature that is more conforming to light output color temperature of the conflicting user lighting need than the first lighting color temperature is to the light color temperature of the conflicting user lighting need.

In some embodiments, the second lighting has a second lighting light output intensity that is less conforming to the light output intensity of the conflicting user lighting need than the first light output intensity is to the light output intensity of the conflicting user lighting need.

In some embodiments, the second lighting includes a face first lighting component having a face first light intensity and a face first color temperature and a task first lighting component having a task first light intensity and a task first color temperature. In some versions of those embodiments the task first light intensity is more conforming to the light output intensity of the conflicting user lighting need than the face first light intensity is to the light output intensity of the conflicting user lighting need. In some versions of those embodiments the task first color temperature is more conforming to the color temperature of the conflicting user lighting need than the face first color temperature is to the light output intensity of the conflicting user lighting need.

In some embodiments, the second lighting is provided after the first user and the conflicting user are within a predefined distance of one another for a predefined amount of time.

In some embodiments, the second lighting is provided on an intermittent basis. Also, the second lighting may have a spectral power distribution that is increased in at least one of the blue-green region and the yellow-red region relative to the first lighting.

In some embodiments, the method further includes the step of setting the second light output intensity of the second lighting to achieve the first user lighting need at the second lighting color temperature.

Generally, in another aspect, a method of providing individualized lighting settings in a lighting system is provided and includes the steps of: identifying a first user position of a first user; identifying first user information indicative of first user biological lighting needs of the first user; identifying a second user position of a second user; identifying second user information indicative of second user biological lighting needs of the second user that are distinct from the first user biological lighting needs; comparing the first user position to the second user position; and determining a first lighting setting for the first user and a second lighting setting for the second user when the first user position and the second user position are within a predefined distance. The first lighting setting and the second lighting setting are chosen to reduce contrast between the first lighting setting and the second lighting setting via reduction of light intensity differential between the first lighting setting and the second lighting setting, while setting color temperatures for each of the first lighting setting and the second lighting setting to maintain respective of the first user biological lighting needs and the second user biological lighting needs.

Generally, in another aspect, a method of providing individualized lighting settings in a lighting system is provided and includes the step of: identifying a first user position of a first user; identifying first user information indicative of first user biological lighting needs of the first user; identifying a second user position of a second user; identifying second user information indicative of second user biological lighting needs of the second user that are distinct from the first user biological lighting needs; comparing the first user position to the second user position; and determining a first lighting setting for the first user and a second lighting setting for the second user when the first user position and the second user position are within a predefined distance. The first lighting setting and the second lighting setting are chosen to reduce contrast between the first lighting setting and the second lighting setting via reduction of color temperature differential between the first lighting setting and the second lighting setting, while setting light intensity for each of the first lighting setting and the second lighting setting to maintain respective of the first user biological lighting needs and the second user biological lighting needs.

Generally, in another aspect, a method of providing individualized lighting settings in a lighting system is provided and includes the steps of: identifying first user lighting information indicative of first user lighting needs of a first user, the first user lighting needs indicative of a first light intensity at a reference color temperature and a first color temperature at a reference light intensity; identifying second user lighting information indicative of second user lighting needs of a second user, the second user lighting needs indicative of a second light intensity at the reference color temperature and a second color temperature at the reference light intensity; and providing a first lighting having a first light characteristic to the first user and simultaneously providing a second lighting having a second light characteristic to the second user when the first user and the second user are within a predefined distance and when variation between the first user lighting needs and the second user lighting needs is outside of a predefined variation. The first light characteristic includes an actual first light intensity and an actual modified first color temperature, the second light characteristic includes an actual second light intensity and an actual second color temperature, the modified light intensity absolute difference between the actual first light intensity and the actual second light intensity is less than an original light intensity absolute difference between the first light intensity and the second light intensity, and a modified color temperature absolute difference between the actual first color temperature and the actual second color temperature is more than an original color temperature absolute difference between the first color temperature and the second color temperature.

Generally, in another aspect, a method of providing individualized lighting settings in a lighting system is provided and includes the steps of: identifying first user lighting information indicative of first user lighting needs of a first user, the first user lighting needs indicative of a first light intensity at a reference color temperature and a first color temperature at a reference light intensity; identifying second user lighting information indicative of second user lighting needs of a second user, the second user lighting needs indicative of a second light intensity at the reference color temperature and a second color temperature at the reference light intensity; and providing a first lighting having a first light characteristic to the first user and simultaneously providing a second lighting having a second light characteristic to the second user when the first user and the second user are within a predefined distance and when variation between the first user lighting needs and the second user lighting needs is outside of a predefined variation. The first light characteristic includes an actual first light intensity and an actual modified first color temperature, the second light characteristic includes an actual second light intensity and an actual second color temperature, a modified color temperature absolute difference between the actual first color temperature and the actual second color temperature is less than an original color temperature absolute difference between the first color temperature and the second color temperature, and a modified light intensity absolute difference between the actual first light intensity and the actual second light intensity is more than an original light intensity absolute difference between the first light intensity and the second light intensity.

Other embodiments may include a non-transitory computer readable storage medium storing instructions executable by a processor to perform a method such as one or more of the methods described herein. Yet another implementation may include a system including memory and one or more processors operable to execute instructions, stored in the memory, to perform a method such as one or more of the methods described herein.

As used herein for purposes of the present disclosure, the term "LED" should be understood to include any electroluminescent diode or other type of carrier injection/junction-based system that is capable of generating radiation in response to an electric signal. Thus, the term LED includes, but is not limited to, various semiconductor-based structures that emit light in response to current, light emitting polymers, organic light emitting diodes (OLEDs), electroluminescent strips, and the like. In particular, the term LED refers to light emitting diodes of all types (including semi-conductor and organic light emitting diodes) that may be configured to generate radiation in one or more of the infrared spectrum, ultraviolet spectrum, and various portions of the visible spectrum (generally including radiation wavelengths from approximately 400 nanometers to approximately 700 nanometers). Some examples of LEDs include, but are not limited to, various types of infrared LEDs, ultraviolet LEDs, red LEDs, blue LEDs, green LEDs, yellow LEDs, amber LEDs, orange LEDs, and white LEDs (discussed further below). It also should be appreciated that LEDs may be configured and/or controlled to generate radiation having various bandwidths (e.g., full widths at half maximum, or FWHM) for a given spectrum (e.g., narrow bandwidth, broad bandwidth), and a variety of dominant wavelengths within a given general color categorization.

For example, one implementation of an LED configured to generate essentially white light (e.g., a white LED) may include a number of dies which respectively emit different spectra of electroluminescence that, in combination, mix to form essentially white light. In another implementation, a white light LED may be associated with a phosphor material that converts electroluminescence having a first spectrum to a different second spectrum. In one example of this implementation, electroluminescence having a relatively short wavelength and narrow bandwidth spectrum "pumps" the phosphor material, which in turn radiates longer wavelength radiation having a somewhat broader spectrum.

It should also be understood that the term LED does not limit the physical and/or electrical package type of an LED. For example, as discussed above, an LED may refer to a single light emitting device having multiple dies that are configured to respectively emit different spectra of radiation (e.g., that may or may not be individually controllable). Also, an LED may be associated with a phosphor that is considered as an integral part of the LED (e.g., some types of white LEDs). In general, the term LED may refer to packaged LEDs, non-packaged LEDs, surface mount LEDs, chip-on-board LEDs, T-package mount LEDs, radial package LEDs, power package LEDs, LEDs including some type of encasement and/or optical element (e.g., a diffusing lens), etc.

The term "light source" should be understood to refer to any one or more of a variety of radiation sources, including, but not limited to, LED-based sources (including one or more LEDs as defined above), incandescent sources (e.g., filament lamps, halogen lamps), fluorescent sources, phosphorescent sources, high-intensity discharge sources (e.g., sodium vapor, mercury vapor, and metal halide lamps), lasers, and various types of electroluminescent sources, including luminescent polymers.

A given light source may be configured to generate electromagnetic radiation within the visible spectrum, outside the visible spectrum, or a combination of both. Hence, the terms "light" and "radiation" are used interchangeably herein. Additionally, a light source may include as an integral component one or more filters (e.g., color filters), lenses, or other optical components. Also, it should be understood that light sources may be configured for a variety of applications, including, but not limited to, indication, display, and/or illumination. An "illumination source" is a light source that is particularly configured to generate radiation having a sufficient intensity to effectively illuminate an interior or exterior space. In this context, "sufficient intensity" refers to sufficient radiant power in the visible spectrum generated in the space or environment (the unit "lumens" often is employed to represent the total light output from a light source in all directions, in terms of radiant power or "luminous flux") to provide ambient illumination (i.e., light that may be perceived indirectly and that may be, for example, reflected off of one or more of a variety of intervening surfaces before being perceived in whole or in part).

The term "spectrum" should be understood to refer to any one or more frequencies (or wavelengths) of radiation produced by one or more light sources. Accordingly, the term "spectrum" refers to frequencies (or wavelengths) not only in the visible range, but also frequencies (or wavelengths) in the infrared, ultraviolet, and other areas of the overall electromagnetic spectrum. Also, a given spectrum may have a relatively narrow bandwidth (e.g., a FWHM having essentially few frequency or wavelength components) or a relatively wide bandwidth (several frequency or wavelength components having various relative strengths). It should also be appreciated that a given spectrum may be the result of a mixing of two or more other spectra (e.g., mixing radiation respectively emitted from multiple light sources).

For purposes of this disclosure, the term "color" is used interchangeably with the term "spectrum." However, the term "color" generally is used to refer primarily to a property of radiation that is perceivable by an observer (although this usage is not intended to limit the scope of this term). Accordingly, the terms "different colors" implicitly refer to multiple spectra having different wavelength components and/or bandwidths. It also should be appreciated that the term "color" may be used in connection with both white and non-white light.

The term "color temperature" generally is used herein in connection with white light, although this usage is not intended to limit the scope of this term. Color temperature essentially refers to a particular color content or shade (e.g., reddish, bluish) of white light. The color temperature of a given radiation sample conventionally is characterized according to the temperature in degrees Kelvin (K) of a black body radiator that radiates essentially the same spectrum as the radiation sample in question. Black body radiator color temperatures generally fall within a range of from approximately 700 degrees K (typically considered the first visible to the human eye) to over 10,000 degrees K; white light generally is perceived at color temperatures above 1500-2000 degrees K.

Lower color temperatures generally indicate white light having a more significant red component or a "warmer feel," while higher color temperatures generally indicate white light having a more significant blue component or a "cooler feel." By way of example, fire has a color temperature of approximately 1,800 degrees K, a conventional incandescent bulb has a color temperature of approximately 2848 degrees K, early morning daylight has a color temperature of approximately 3,000 degrees K, and overcast midday skies have a color temperature of approximately 10,000 degrees K. A color image viewed under white light having a color temperature of approximately 3,000 degree K has a relatively reddish tone, whereas the same color image viewed under white light having a color temperature of approximately 10,000 degrees K has a relatively bluish tone.

The terms "lighting fixture" and "luminaire" are used interchangeably herein to refer to an implementation or arrangement of one or more lighting units in a particular form factor, assembly, or package. The term "lighting unit" is used herein to refer to an apparatus including one or more light sources of same or different types. A given lighting unit may have any one of a variety of mounting arrangements for the light source(s), enclosure/housing arrangements and shapes, and/or electrical and mechanical connection configurations. Additionally, a given lighting unit optionally may be associated with (e.g., include, be coupled to and/or packaged together with) various other components (e.g., control circuitry) relating to the operation of the light source(s). An "LED-based lighting unit" refers to a lighting unit that includes one or more LED-based light sources as discussed above, alone or in combination with other non LED-based light sources. A "multi-channel" lighting unit refers to an LED-based or non LED-based lighting unit that includes at least two light sources configured to respectively generate different spectrums of radiation, wherein each different source spectrum may be referred to as a "channel" of the multi-channel lighting unit.

The term "controller" is used herein generally to describe various apparatus relating to the operation of one or more light sources. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

In one network implementation, one or more devices coupled to a network may serve as a controller for one or more other devices coupled to the network (e.g., in a master/slave relationship). In another implementation, a networked environment may include one or more dedicated controllers that are configured to control one or more of the devices coupled to the network. Generally, multiple devices coupled to the network each may have access to data that is present on the communications medium or media; however, a given device may be "addressable" in that it is configured to selectively exchange data with (i.e., receive data from and/or transmit data to) the network, based, for example, on one or more particular identifiers (e.g., "addresses") assigned to it.

The term "network" as used herein refers to any interconnection of two or more devices (including controllers or processors) that facilitates the transport of information (e.g. for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, a mouse, keyboard, keypad, various types of game controllers (e.g., joysticks), track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

Figure 1:
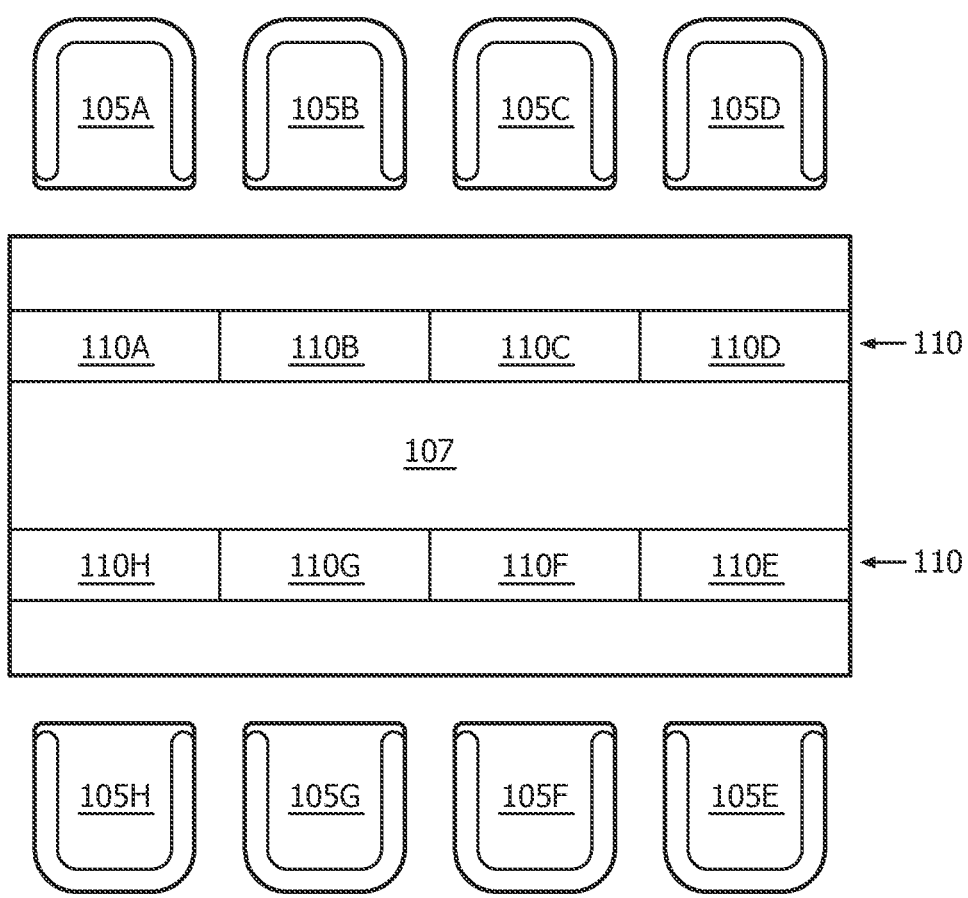
FIG. 1 illustrates a top plan view of a meeting room with an embodiment of a lighting fixture positioned above a table in the meeting room.

User-responsive lighting systems have been implemented where users carry a personal device that communicates their lighting needs to the lighting system. The light output of one or more lighting fixtures in the lighting environment may be adjusted in response to a user's lighting preferences based on their lighting needs. Although such systems enable adjustment of a lighting fixture based on the individual settings of a user, they may have one or more drawbacks. For example, in some environments User-responsive lighting systems may not enable freedom of movement while maintaining lighting preferences. Also, for example, in some environments where multiple users interact, closely positioned users with differing lighting needs may not be supplied with individualized lighting zones that lessen contrast between the individualized lighting zones.

Various therapeutic lighting systems have also been implemented. Such therapeutic lighting systems often include a lighting fixture that a user must sit or stand in front of for a period of time for therapy purposes. Such therapeutic lighting systems may have one or more drawbacks such as, for example, the requirement of dedicated spaces or locations for use and/or the bright therapeutic light being bothersome to other individuals present in proximity that have other lighting needs. Thus, Applicants have recognized and appreciated a need to provide methods and apparatus related to lighting that may compensate for varying lighting needs of adjacent users to lessen contrast between the lighting provided to the adjacent users while maintaining benefits of separate users' lighting preferences.

More generally, Applicants have recognized and appreciated that it would be beneficial to provide lighting methods and apparatus for providing personalized lighting to users positioned proximal to one another.

In view of the foregoing, various embodiments and implementations of the present invention are directed to lighting control and lighting apparatus.

In the following detailed description, for purposes of explanation and not limitation, representative embodiments disclosing specific details are set forth in order to provide a thorough understanding of the claimed invention. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatus and methods may be omitted so as to not obscure the description of the representative embodiments. Such methods and apparatus are clearly within the scope of the claimed invention. For example, various embodiments of the approach disclosed herein are particularly suited for a lighting system that includes a vertical face lighting component, a horizontal task lighting component, and at least one sensor to detect the presence and/or position of a user. Accordingly, for illustrative purposes, the claimed invention is discussed in conjunction with such a lighting system. However, other configurations and applications are contemplated without deviating from the scope or spirit of the claimed invention. For example, aspects may be implemented in other lighting systems that only include a task lighting component or only include a face lighting component.

Referring to FIG. 1, a top plan view of a meeting room is illustrated. Inside the meeting room are eight chairs 105A-H positioned around a rectangular table 107. A lighting system having a lighting fixture 110 is present in the meeting room positioned above the rectangular table 107. Lighting fixture 110 includes eight individual lighting zones 110A-H. Each of the lighting zones 110A-H may optionally be independently controlled and allow for adjustments to one or more light output characteristics of generated light output such as the intensity, color, and/or color temperature. For example, the light intensity, color, and/or color temperature of the light output generated by lighting zone 110A may be independently adjusted and the light intensity, color, and/or color temperature of the light output generated by lighting zone 1106 may be separately independently adjusted.

Figure 2:
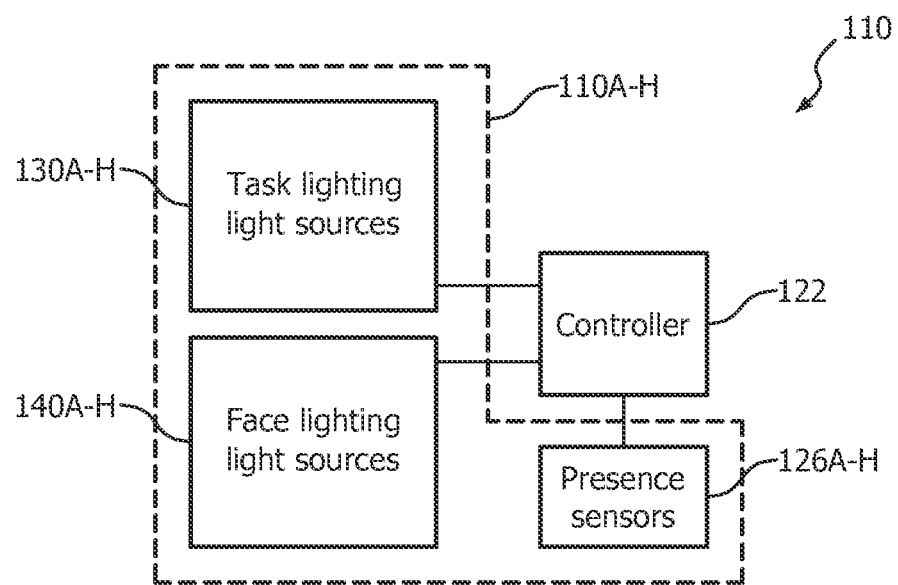
FIG. 2 illustrates a block diagram of the lighting fixture of FIG. 1.

Referring to FIG. 2, a block diagram of the lighting fixture 110 is illustrated. The lighting zones 110A-H include task lighting light sources 130A-H, face lighting light sources 140A-H, and presence sensors 126A-H. At least one controller 122 is in communication with the lighting zones 110A-H and the presence sensors 126A-H and controls the lighting zones 110A-H based at least in part on input received via the presence sensors 126A-H. The task lighting light sources 130A-H each contain one or more light sources that selectively generate light output that is directed toward and illuminates at least a portion of the table 107. The face lighting light sources 140A-H each contain one or more light sources that selectively generate light output that is directed toward and illuminates at least a portion of the area adjacent to respective of chairs 105A-H (e.g., at least the area that would be occupied by faces of humans that are sitting in the chairs 105A-H). In some embodiments the light sources may include LEDs. In some embodiments a single light source may generate task lighting and face lighting.

The controller 122 controls the status of the task lighting light sources 130A-H and the face lighting light sources 140A-H. For example, the controller 122 may be in communication with one or more drivers powering task lighting light sources 130A-H to control whether each of the task lighting light sources 130A-H is generating light output and, if generating light output, to optionally control one or more characteristics of the light output generated by the respective task lighting light sources 130A-H. Additionally, for example, the controller 122 may be in communication with one or more drivers powering the face lighting light sources 140A-H to control whether the face lighting light sources 140A-H generate light output and, if generating light output, to optionally control one or more characteristics of the light output generated by the respective face lighting light sources 140A-H.

Generally speaking, each of the presence sensors 126A-H may be provided in combination with one of the individual lighting zones 110A-H and may detect the presence of a user in the vicinity of a respective of the individual lighting zones 110A-H. For example, the presence sensors 126A-H may each include a passive Infrared (PIR) sensor having a field of view generally directed toward the area in which light output would be provided by a respective of the individual lighting zones 110A-H. In some embodiments a single presence sensor may detect presence for multiple lighting zones 110A-H. For example, in some embodiments a single presence sensor may be provided that detects presence in all lighting zones 110A-H. Also, for example, in some embodiments a first presence sensor may be provided that detects presence in all lighting zones 110A-B and a second presence sensor may be provided that detects presence in lighting zones 110C-D.

Also, for example, the presence sensors 126A-H may optionally include one or more sensors utilized to directly or indirectly determine the location of one or more users. For example, the presence sensors 126A-H may include one or more radars, cameras, distance sensors, and/or PIR sensors. For example, a radar may be utilized to detect the location of a personal device carried by a user (e.g., based on detection of RF signals emitted by the personal device and/or RF signals emitted by the radar) and it may be assumed that the location of the personal device corresponds to the location of the user. Also, for example, a camera and a distance sensor may be utilized to identify a location of a particular user based on facial recognition and a distance reading from the distance sensor. In some embodiments the presence sensors 126A-H may be omitted. For example, in embodiments location data for a user may be received via input from personal devices of users (e.g., via a GPS device and/or other location device of the personal devices) and the presence sensors 126A-H may optionally be omitted.

The presence sensors 126A-H and/or other device (e.g., a separate receiver in communication with the controller 122) may also optionally receive lighting needs data from users indicative of the lighting needs of those users. For example, a user may have an electronic personal device such as a smart phone, a tablet computer, a dedicated lighting device, and/or other device that transmits lighting information concerning the lighting preferences associated with the user. For example, for a user who prefers biologically stimulating lighting during certain times, biologically relaxing lighting during certain times, and/or biologically neutral lighting during certain times, the personal device of that user may provide a signal that is indicative of such (e.g., by indicating a lighting type preference; by indicating color temperature, color, and/or intensity preferences; by indicating a travel schedule that may be utilized to determine lighting preferences; and/or by indicating a sleep schedule that may be utilized to determine lighting preferences).

Figure 3:
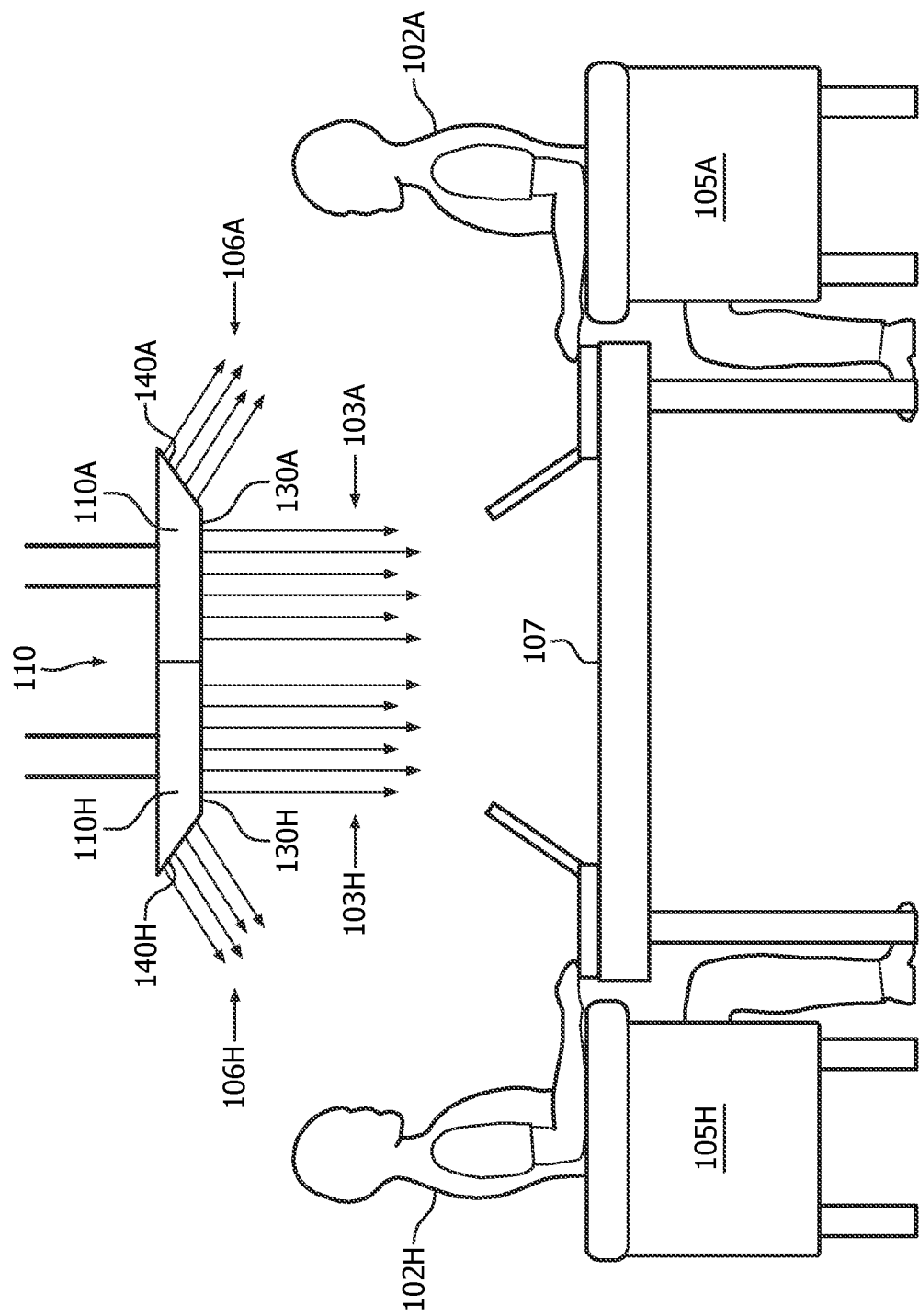
FIG. 3 illustrates a side view of the table and lighting fixture of FIG. 1; a first user and a second user are present in chairs provided around the table.

Each of the lighting zones 110A-H may direct light output toward a most closely adjacent of the chairs 105A-H and/or toward an area of the table 107 located generally under the respective of the lighting zones 110A-H. For example, referring to FIG. 3, a side view of table 107, chairs 105A, 105H, and lighting zones 110A, 110H is illustrated. A first user 102A is present in chair 105A and a second user 102H is present in chair 105H.

Lighting zone 110A is generating light output having a vertical lighting component 106A (via face lighting light sources 140A) and a horizontal lighting component 103A (via task lighting light sources 130A). The vertical lighting component 106A is generally directed toward the chair 105A and toward the face of the first user 102A. The horizontal lighting component 103A is generally directed toward the table 107 below the lighting zone 110A. Lighting zone 110H is generating light output having a vertical lighting component 106H (via face lighting light sources 140H) and a horizontal lighting component 103H (via face lighting light sources 130H). The vertical lighting component 106H is generally directed toward the chair 105H and toward the face of the second user 102H. The horizontal lighting component 103H is generally directed toward the table 107 below the lighting zone 110H.

In some implementations the vertical lighting components 106A and/or 106H may have narrow beam angles to lessen the visibility of the face lighting to a neighboring user. In FIG. 2 the vertical lighting components 106A and 106H are directed to different areas (faces of different users 102A, 102H) and have no interference between one another. Horizontal lighting components 103A and 103H are directed toward the same general task area and may have some overlap with one another and/or have some light output in close proximity with one another. The light output from lighting zones 110A and/or 110H may be adjusted to provide a desired light output to users 102A and/or 102E.

For example, in some implementations the light output characteristics of the face lighting provided to a user via vertical lighting components 106A or 106H and/or the light output characteristics of the task lighting provided via horizontal lighting components 103A or 103H may be individually tunable. One or more of the lighting components 103A, 103H, 106A, 106H may have one or more independently controllable light output characteristics such as intensity, color, and/or color temperature. In some implementations, the lighting preferences of users 102A, 102H may be represented by the respective vertical lighting component 106A, 106H, horizontal lighting component 103A, 103H, and/or a combination of both horizontal and vertical lighting components.

In some implementations the ratio of vertical lighting to horizontal lighting may be changed for a user in a single area to match the user's lighting preferences while minimizing interference with lighting preferences of one or more other users. For example, in some embodiments if user 102A desires a biologically stimulating light (e.g., high intensity level) and user 102H desires a biologically relaxing light (e.g., low intensity level), the differences in the horizontal lighting components 103A and 103H may be minimalized to create little noticeable difference between the two lighting components, while the vertical lighting components 106A and 106H may be configured to provide the appropriate stimulating light (e.g., vertical lighting component 106A having high intensity and vertical lighting component 106H having low intensity). Due to the particularized and distinct directions of the vertical lighting components 106A and 106H, differences in lighting between the two components may be less noticeable than any differences between the horizontal lighting components 103A and 103H.

In some implementations the face lighting light sources 140A-H may each illuminate a relatively small area using a narrow beam. For example, face lighting light sources 140A-H may generate a light output having a beam width of approximately ten degrees that illuminates a user's face while not illuminating a significant area outside of the user's face. In some implementations the lighting system may optionally include a sensor that may recognize the position of a user's face. In some versions of those implementations the lighting system may maintain the face lighting on the user's face when the user moves locally while continuing to be situated in the same general lighting area. For example, if a user adjusts his chair, thereby readjusting the location of his face slightly, the sensor may detect this movement and readjust the face lighting slightly to maintain illumination of the user's face. In some of those implementations if the user exits the lighting area (e.g., gets up from the table and walks to a different area of the room), the lighting beam may not continue to follow the user and/or another lighting fixture in the room may be activated and/or adjusted to provide the appropriate lighting.

In some implementations, when two neighboring users have differing lighting needs, contrast between the lighting provided to the two users may be reduced by making the difference smaller between two light outputs applied to the users with respect to illumination intensity but by making the difference larger between the two light outputs with respect to color temperature. For example, if user 102A desires stimulating light and user 102H desires light having a neutral setting, then the illumination intensity of lighting components 103A and/or 106A may be substantially the same as respective of lighting components 103H and/or 106H and may be set to an illumination intensity so as to provide neutral lighting at a color temperature range of 3000K to 4000K (e.g., approximately 225 lux). The color temperature of the lighting components 103H and/or 106H may be set approximately within the range of 3000K to 4000K to achieve neutral lighting for the user 102H. In some implementations the color temperature of the lighting components 103A and/or 106A may be increased to increase the stimulating effect of the light at the lower illumination intensity level (e.g., approximately 225 lux). For example, the color temperature of the lighting components 103A and/or 106A may be set to approximately 5000K.

In some implementations the lighting components 103A and/or 106A may additionally and/or alternatively be provided with a spectral power distribution that is more concentrated in one or more color region such as the blue-green region to increase the biologically stimulating nature of the light. In some implementations the lighting components 103H and/or 106H may additionally and/or alternatively be provided with a spectral power distribution that is more concentrated in one or more color region such as the yellow-red region to increase the biologically relaxing nature of the light. For example, in some embodiments the color temperature of the lighting components 103A and/or 106A may be increased to increase the stimulating effect of the light and the spectral power distribution may be more concentrated in the blue-green region to increase the biologically stimulating nature of the light. The amount of color temperature increase needed to achieve the biologically stimulating light may be lessened by increasing the spectral power distribution in the blue-green region. Also, the amount of color temperature decrease needed to achieve biologically stimulating light may be lessened by increasing the spectral power distribution in the yellow-red region.

In some implementations, when two neighboring users have differing lighting needs, contrast between the lighting provided to the two users may be reduced by making the difference smaller between two light outputs applied to the users with respect to color temperature but by making the difference larger between the two light outputs with respect to illumination intensity. For example, if user 102A desires stimulating light and user 102H desires light having a neutral setting, then the color temperature of lighting components 103A and/or 106A may be substantially the same as respective of lighting components 103H and/or 106H and may be set to a color temperature so as to provide neutral lighting at an illumination intensity of approximately 200 to 300 lux (e.g., approximately 3000K to 4000K). The illumination intensity of the lighting components 103H and/or 106H may be set approximately at 225 lux to achieve neutral lighting for the user 102H. In some implementations the illumination intensity of the lighting components 103A and/or 106A may be increased to increase the stimulating effect of the light at the selected color temperature (e.g., approximately 3000K to 4000K). For example, the illumination intensity of the lighting components 103A and/or 106A may be set to approximately 350 lux.

In some implementations the lighting components 103A and/or 106A may additionally and/or alternatively be provided with a spectral power distribution that is more concentrated in one or more color region such as the blue-green region to increase the biologically stimulating nature of the light. In some implementations the lighting components 103H and/or 106H may additionally and/or alternatively be provided with a spectral power distribution that is more concentrated in one or more color region such as the yellow-red region to increase the biologically relaxing nature of the light. For example, in some embodiments the intensity of the lighting components 103A and/or 106A may be increased to increase the stimulating effect of the light and the spectral power distribution may be more concentrated in the blue-green region to increase the biologically stimulating nature of the light. The amount of intensity increase needed to achieve the biologically stimulating light may be lessened by increasing the spectral power distribution in the blue-green region. Also, the amount of intensity decrease needed to achieve biologically stimulating light may be lessened by increasing the spectral power distribution in the yellow-red region.

Figure 4:
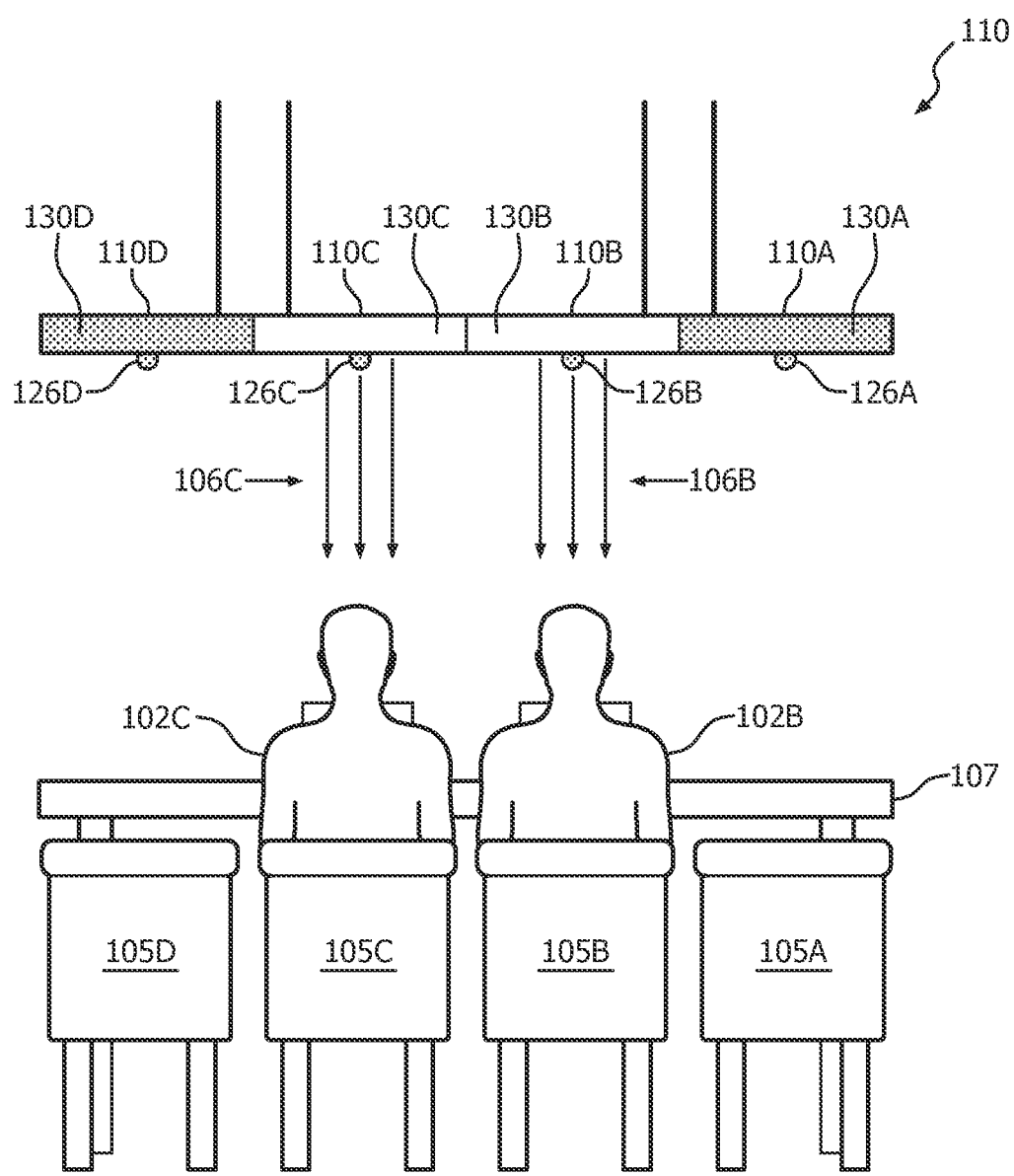
FIG. 4 illustrates another side view of the table and lighting fixture of FIG. 1; a third user and a fourth user are present in chairs provided around the table.

Also, for example, referring to FIG. 4, a view of table 107, chairs 105A-D, and lighting zones 110A-D is illustrated. A third user 102B is present in chair 105B and a fourth user 102C is present in chair 105C. Vertical lighting component 106B of lighting zone 1106 is directed toward the face of user 102B and vertical lighting component 106C of lighting zone 110C is directed toward the face of user 102C.

As an example, assume user 102B desires stimulating light having a preferred stimulating intensity, preferred stimulating color, and/or preferred stimulating color temperature and user 102C desires relaxing light having a preferred relaxing intensity, preferred relaxing color, and/or preferred relaxing color temperature. Since user 102B and 102C are in close proximity to one another, then a light output may be generated such that a ratio of the light intensity of the vertical lighting component 106B relative to the light intensity of vertical lighting component 106C is less than a ratio of the preferred stimulating intensity relative to the preferred relaxing intensity. In other words, the difference between the preferred intensities in one or more wavelengths is reduced in the generated lighting components 106B, 106C (e.g., via reduction of the preferred stimulating intensity and/or increase of the preferred relaxing intensity). The generated light output may also be such that a ratio of the color temperature of the vertical lighting component 106B relative to the color temperature of vertical lighting component 106C is greater than a ratio of the preferred stimulating color temperature relative to the preferred relaxing color temperature. In other words, the difference between the preferred color temperatures may be increased in the generated lighting components 106B, 106C (e.g., via increase of the preferred stimulating color temperature and/or decrease of the preferred relaxing color temperature). Generally speaking, a given biological stimulation at a given lux may be maintained when the lux is decreased by increasing the color temperature. For example, the biological effect obtained at 4000 lux and 4000 K may be substantially equivalent to the biological effect obtained at 2100 lux and 17000 K. In some implementations the correlation between lux and color temperature to achieve a given biological effect is generally logarithmic in nature. In some implementations the lighting component 106B may additionally and/or alternatively be provided with a spectral power distribution that is more concentrated in the blue-green region to increase the biologically stimulating nature of the light. In some implementations the lighting component 106C may additionally and/or alternatively be provided with a spectral power distribution that is more concentrated in the yellow-red region to increase the biologically relaxing nature of the light.

As another example, assume user 102B desires stimulating light having a preferred stimulating intensity, preferred stimulating color, and/or preferred stimulating color temperature and user 102C desires relaxing light having a preferred relaxing intensity, preferred relaxing color, and/or preferred relaxing color temperature. In some embodiments a light output may be generated such that a ratio of the color temperature of the vertical lighting component 106B relative to the color temperature of the vertical lighting component 106C is less than a ratio of the preferred stimulating color temperature relative to the preferred relaxing color temperature. In other words, the difference between the color temperatures is reduced in the generated lighting components 106B, 106C (e.g., via reduction of the preferred stimulating color temperature and/or increase of the preferred relaxing color temperature). The generated light output may also be such that a ratio of the illumination intensity of the vertical lighting component 106B relative to the illumination intensity of vertical lighting component 106C is greater than a ratio of the preferred stimulating illumination intensity relative to the preferred relaxing illumination intensity. In other words, the difference between the illumination intensities may be increased in the generated lighting components 106B, 106C (e.g., via increase of the preferred stimulating illumination intensity and/or decrease of the preferred relaxing illumination intensity). Generally speaking, a given biological stimulation at a given color temperature may be maintained when the color temperature is decreased by increasing the illumination intensity. For example, the biological effect obtained at 2100 lux and 17000 K may be substantially equivalent to the biological effect obtained at 4000 lux and 4000 K. In some implementations the lighting component 106B may additionally and/or alternatively be provided with a spectral power distribution that is more concentrated in the blue-green region to increase the biologically stimulating nature of the light. In some implementations the lighting component 106C may additionally and/or alternatively be provided with a spectral power distribution that is more concentrated in the yellow-red region to increase the biologically relaxing nature of the light.

In some implementations, any applied biological stimulating light may additionally and/or alternatively be locally applied to a user with biologically stimulating needs in a periodic manner. For example, in some embodiments applied biological stimulating light may be applied for approximately five minutes each half hour (either in a continuous five minute increment or spread intermittently across the half hour such as for ⅙ of every second for a half hour).

In some implementations of lighting systems that have both face lighting and task lighting components the differences in face lighting between users positioned close to one another may be increased while the differences in task lighting between those users is minimized. For example, one of the face lighting components may contain increased blue-green spectral power distribution (relative to the spectral power distribution of the task lighting component) that may benefit a user with biological stimulating lighting needs. Also, for example, one of the face lighting components may additionally and/or alternatively contain increased yellow-red spectral power distribution (relative to the spectral power distribution of the task lighting component) that may benefit a user with biological relaxing lighting needs. Also, for example, the face lighting components may additionally and/or alternatively have larger differences in light output intensity and/or color temperature than the task lighting components.

In some implementations, the user may have the option to manually alter one or more light output characteristics of light applied to the user. For example, a user may have the option to manually alter the intensity and/or color temperature of his lighting components using manual controls. In some implementations the lighting controls may be accessible via an electronic personal device of the user, which then may relay the changes to the controller 122 (e.g., via a network connection). In other implementations the controls to manually alter the lighting effects of the user's lighting settings may be directly in connection with the controller 122 through a device present in the room with the user. For example, each user may have a device in the vicinity of his seat at table 107 which may give the user options for fine tuning the intensity and/or color temperature of his lighting components.

Figure 5:
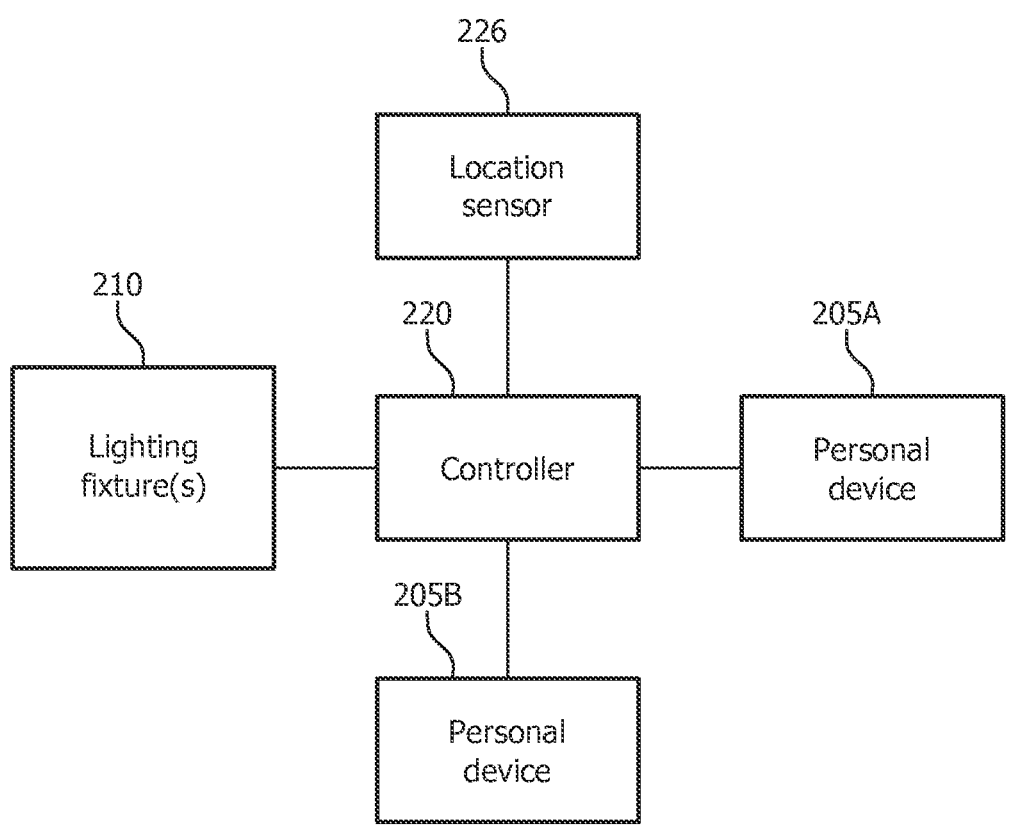
FIG. 5 illustrates a block diagram of an embodiment of a lighting system.

Referring to FIG. 5, another embodiment of a lighting system is illustrated. The lighting system includes a controller 220 in communication with a presence sensor 226 and in communication with one or more lighting fixtures 210. The controller 220 is also in communication with personal devices 205A, 205B of two separate users. In some implementations the controller 220 and/or the location sensor 226 may be integrated with one or more of the lighting fixtures 210. For example, in some embodiments multiple lighting fixtures 210 may be provided, each having a controller integrated therein and controllers across multiple lighting fixtures 210 may optionally communicate with one another. Also, for example, in some embodiments multiple lighting fixtures 210 may be provided, with one having a controller integrated therein that controls multiple lighting fixtures 210 via network communication with those other lighting fixtures.

The lighting fixtures 210 may include one or more lighting fixtures that generate light with unique light output characteristics and/or that alter light output characteristics of light thereof responsive to communications from controller 220. For example, in some embodiments the lighting fixture 210 may include a first lighting fixture and a second lighting fixture. The first lighting fixture may generate a first light output having first light output characteristics in a first area in response to communications from controller 220. The second lighting fixture may generate a distinct second light output having second light output characteristics in a second area in response to communications from controller 220. In some embodiments the first and/or the second lighting fixture may have adjustable light output characteristics such as light output level, color, color temperature, and/or beam shape. The area(s) in which a lighting fixture provides light output may be fixed (e.g., as a function of the installation location of the lighting fixtures) or may be adjustable. Adjustability of the areas in which a lighting fixture provides light output may be achieved utilizing one or more of a variety of methods and/or apparatus. For example, adjustability may be achieved by turning on/off one of multiple light sources in the lighting fixture; by mechanically adjusting the position and/or orientation of the entire lighting fixture; and/or by mechanically adjusting the position and/or orientation of a light source and/or an optical element (e.g., a reflector, a refractor) of the lighting fixture.

In some implementations the lighting fixtures 210 may include a LED-based lighting fixture having a plurality of LEDs that may be individually turned on/off, individually dimmed, and/or individually tuned (e.g., tunable color, beam shape, beam size). A first group of the LEDs of the LED-based lighting fixture may be adjusted to achieve a light output having first light output characteristics and a second LED group of the LED-based lighting fixture may be adjusted to achieve a light output having second light output characteristics. In some embodiments the lighting fixtures 210 may include a plurality of light emitting ceiling tile groups, with each group containing one or more tiles (e.g., tiles with implemented LEDs) and having a unique lighting setting. Examples of specific lighting fixture implementations are provided herein. One of ordinary skill in the art, having had the benefit of the present disclosure, will recognize and appreciate that in other embodiments additional and/or alternative lighting fixtures may be utilized in the lighting systems and/or lighting methods described herein.

The location sensor 226 may include one or more sensors utilized to determine the location of one or more users. For example, the location sensor 226 may include one or more radars, cameras, distance sensors, and/or PIR sensors. For example, a radar may be utilized to detect the location of the personal device 205A (e.g., based on detection of RF signals emitted by the personal device and/or RF signals emitted by the radar) and it may be assumed that the location of the personal device 205A corresponds to the location of a first user. Also, for example, a camera and a distance sensor may be utilized to identify a location of a particular user based on facial recognition and a distance reading from the distance sensor. In some embodiments the location sensor 226 may be omitted. For example, in embodiments of the lighting system location data may be received via input from personal devices 205A, 205B (e.g., via a GPS device and/or other location device of the personal devices 205A, 205B) and the location sensor 226 may optionally be omitted.

In some embodiments, the personal devices 205A, 205B may include a lighting token carried by a user that enables communication of information relevant to the lighting needs of the user. For example, in some embodiments the personal devices 205A, 205B may include a RFID tag carried by the user that may be read by a RFID receiver to identify the lighting needs of the user. For instance, the RFID tag may communicate the identity of the user to the controller 220. The controller 220 may utilize the identity of the user to retrieve therapeutic lighting settings that are correlated with the user in a database (local database and/or a database accessible via a network). Also, for instance, the RFID tag may communicate the identity of the user to the controller 220; the controller 220 may utilize the identity of the user to retrieve travel history and/or travel plans of the user that are correlated with the user in a database; and based on such travel history and/or travel plans the controller 220 may identify the therapeutic lighting needs of the user.

In some embodiments, the personal devices 205A, 205B may include a smart phone, a tablet computer, and/or other handheld device capable of performing additional functions beyond those described herein. For example, the personal devices 205A, 205B may include a smart phone that communicates therapeutic lighting needs to the controller 220 (either directly or via the supplying of travel itinerary information). In some embodiments the personal devices 205A, 205B may additionally or alternatively communicate location information to the controller 220. For example, the location may be determined at the personal devices 205A, 205B via GPS and/or RF triangulation and such location communicated to the controller 220.

In some embodiments, the personal devices 205A, 205B may include a light sensor to sense if the appropriate lighting effect is present. The readings from the light sensor may optionally be communicated to the controller 220 to optionally modify the light output directed toward the user's location to achieve a desired light output. Also, in some embodiments the readings from the light sensor may be tracked over time and optionally be utilized to determine whether appropriate light effects have been received in a timely manner by the user.

The communication between the various components of the lighting system and/or other devices (e.g., personal devices 205A, 205B) may optionally utilize one or more communications mediums, communications technologies, protocols, and/or inter-process communication techniques. For example, the communication mediums may include any physical medium, including, for example, twisted pair coaxial cables, fiber optics, and/or a wireless link using, for example, infrared, microwave, or encoded visible light transmissions and any suitable transmitters, receivers or transceivers to effectuate communication in the lighting fixture network. Also, for example, the communications technologies may include any suitable protocol for data transmission, including, for example, TCP/IP, variations of Ethernet, Universal Serial Bus, Bluetooth, FireWire, Zigbee, DMX, Dali, 802.11b, 802.11a, 802.11g, token ring, a token bus, serial bus, power line networking over mains or low voltage power lines, and/or any other suitable wireless or wired protocol. For example, in some embodiments the personal devices 205A, 205B may communicate with the controller 220 via RF communications and the controller 220 may communicate with lighting fixtures 210, and/or location sensor 226 via a wired connection.

When controller 220 determines that two (or more) users with conflicting lighting needs are within a predefined distance of one another (e.g., via sensed or obtained location data and/or sensed or obtained lighting need data), individualized lighting may be supplied to the users that may compensate for the varying lighting needs to lessen contrast between the lighting provided to the adjacent users while maintaining benefits of the separate users' lighting preferences. For example, assume a first user desires biologically stimulating light and a second user desires biologically neutral light. In some embodiments the difference between the light intensity of the lighting applied to the two users may be minimalized while the color temperature and/or spectral power distribution of the lighting is adjusted to supply the users with appropriate lighting needs. For instance, second light with a neutral light intensity at approximately 3500 K may be supplied to the second user and first light with the same light intensity, but at approximately 5000 K and/or with a spectral power distribution that is increased in the green-blue region may be supplied to the first user. In some implementations a first of the lighting fixtures 210 may supply the first light and an adjacent of the lighting fixtures 210 may supply the second light. In some implementations a single of the lighting fixtures 210 may supply both the first light and the second light.

Also, for instance first vertical face lighting that is particularized to the first user's lighting needs may be supplied to the first user and second vertical face lighting that is particularized to the second user's lighting needs may be supplied to the second user. Optionally, first horizontal task lighting may additionally be supplied in a task area adjacent the first user and second horizontal task lighting may additionally be supplied in a task area adjacent the second user. The first and second horizontal task lighting may be more conforming to one another than the first and second vertical face lighting. In some implementations multiple lighting fixtures 210 may supply the first and second light. In some implementations a single of the lighting fixtures 210 may supply the first and second light.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

It should also be understood that, unless clearly indicated to the contrary, in any methods claimed herein that include more than one step or act, the order of the steps or acts of the method is not necessarily limited to the order in which the steps or acts of the method are recited. Also, reference numerals appearing in parentheses in the claims, if any, are provided merely for convenience and should not be construed as limiting in any way.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The invention claimed is:

1. A method of providing individualized lighting settings in a lighting system, comprising:
   identifying first user lighting information indicative of first user lighting needs of a first user, said first user lighting needs indicative of a first light intensity at a reference color temperature and a first color temperature at a reference light intensity;
   identifying second user lighting information indicative of second user lighting needs of a second user, said second user lighting needs indicative of a second light intensity at said reference color temperature and a second color temperature at said reference light intensity;
   providing a first lighting having a modified first light characteristic to said first user and simultaneously providing a second lighting having a second light characteristic to said second user when said first user and said second user are within a predefined distance and when variation between said first user lighting needs and said second user lighting needs is outside of a predefined variation;
   wherein said modified first light characteristic includes at least one of a modified first light intensity and a modified first color temperature;
   wherein said second light characteristic includes an emitted second light intensity and an emitted second color temperature;
   wherein said first lighting and said second lighting satisfy either a first condition or a second condition;
   wherein in said first condition a modified light intensity absolute difference between said modified first light intensity and said emitted second light intensity is less than an original light intensity absolute difference between said first light intensity and said second light intensity; and
   wherein in said second condition a modified color temperature absolute difference between said modified first color temperature and said emitted second color temperature is less than an original color temperature absolute difference between said first color temperature and said second color temperature;
   wherein said first lighting includes a face first lighting component having a face first light intensity and a task first lighting component having a task first light intensity; and
   wherein said face first light intensity is closer to said first user lighting needs than said task first light intensity is to said first user lighting needs.

2. The method of claim 1, wherein said modified first light characteristic includes both said modified first light intensity and said modified first color temperature.

3. The method of claim 2, wherein said modified first color temperature is adjusted to maintain said first user lighting needs at said modified first light intensity.

4. The method of claim 1, wherein said second lighting includes a face second lighting component having a face second light intensity and a task second lighting component having a task second light intensity.

5. The method of claim 1, wherein said first lighting is provided on an intermittent basis.

6. The method of claim 1, further comprising identifying a first user position, identifying a second user position, and comparing said first user position to said second user position to determine said predefined distance.

7. The method of claim 1, wherein in said first condition said modified color temperature absolute difference between said modified first color temperature and said modified second color temperature is greater than said original color temperature absolute difference between said first color temperature and said second color temperature.

8. The method of claim 1, wherein in said second condition said modified light intensity absolute difference between said modified first light intensity and said emitted second light intensity is greater than said original light intensity absolute difference between said first light intensity and said second light intensity.

9. A method of providing individualized lighting settings in a lighting system, comprising:
   identifying first lighting to provide to a first user when said first user is not proximal any conflicting lighting users, said first lighting conforming to a first user lighting need of said first user and having a first lighting light output intensity and a first lighting color temperature; and
   providing second lighting to said first user when said first user lighting need is in conflict with a conflicting user lighting need of a conflicting user that is proximal said first user; said second lighting having a second lighting light output intensity that is closer to light output intensity of said conflicting user lighting need than said first lighting light output intensity is to said light output intensity of said conflicting user lighting need;
   wherein said first lighting includes a face first lighting component having a face first light intensity and a task first lighting component having a task first light intensity; and
   wherein said face first light intensity is closer to said first lighting light output intensity than said task first light intensity is to said first lighting light output intensity.

10. The method of claim 9, wherein said second lighting has a second lighting color temperature that is less close to said color temperature of said conflicting user lighting need than said first color temperature is to said color temperature of said conflicting user lighting need.

11. The method of claim 9, wherein said second lighting includes a face first lighting component having a face first light intensity and a face first color temperature and a task first lighting component having a task first light intensity and a task first color temperature.

12. The method of claim 9, wherein said second lighting is provided after said first user and said conflicting user are within a predefined distance of one another for a predefined amount of time.

13. The method of claim 9, wherein said second lighting is provided on an intermittent basis.

14. The method of claim 9, wherein said second lighting has a spectral power distribution that is increased in at least one of the blue-green region and the yellow-red region relative to said first lighting.

15. The method of claim 9, further comprising setting said second lighting color temperature of said second lighting to achieve said first user lighting need at said second lighting light output intensity.

16. A method of providing individualized lighting settings in a lighting system, comprising:
   identifying first lighting to provide to a first user when said first user is not proximal to any conflicting lighting users, said first lighting conforming to a first user lighting need of said first user and having a first lighting light output intensity and a first lighting color temperature; and
   providing second lighting to said first user when said first user lighting need is in conflict with a conflicting user lighting need of a conflicting user that is proximal to said first user;
   said second lighting having a second lighting color temperature that is closer to light output color temperature of said conflicting user lighting need than said first lighting color temperature is to said light color temperature of said conflicting user lighting need,
   wherein said second lighting includes a face first lighting component having a face first light intensity and a face first color temperature and a task first lighting component having a task first light intensity and a task first color temperature.

17. The method of claim 16, wherein said second lighting has a second lighting light output intensity that is less close to said light output intensity of said conflicting user lighting need than said first light output intensity is to said light output intensity of said conflicting user lighting need.

18. The method of claim 16, wherein said second lighting is provided on an intermittent basis.

19. The method of claim 16, wherein said second lighting has a spectral power distribution that is increased in at least one of the blue-green region and the yellow-red region relative to said first lighting.

\* \* \* \* \*